US012751918B2

(12) United States Patent
Rozemberg et al.

(10) Patent No.: US 12,751,918 B2
(45) Date of Patent: Oct. 6, 2026

(54) KETAMINE FORMULATION

(71) Applicant: Fresenius Kabi USA, LLC, Lake Zurich, IL (US)

(72) Inventors: Jessica Rozemberg, Melrose Park, IL (US); Jennifer Gehle-Novak, Melrose Park, IL (US)

(73) Assignee: FRESENIUS KABI USA, LLC, Lake Zurich, IL (US)

( * ) Notice: Subject to any disclaimer, the term of this patent is extended or adjusted under 35 U.S.C. 154(b) by 0 days.

(21) Appl. No.: 19/381,818

(22) Filed: Nov. 6, 2025

(65) Prior Publication Data

US 2026/0124138 A1 May 7, 2026

Related U.S. Application Data

(60) Provisional application No. 63/717,086, filed on Nov. 6, 2024.

(51) Int. Cl.

| | |
|---|---|
| ***A61K 9/08*** | (2006.01) |
| ***A61K 9/00*** | (2006.01) |
| ***A61K 31/135*** | (2006.01) |
| ***A61K 47/02*** | (2006.01) |
| ***A61K 47/22*** | (2006.01) |
| ***A61M 5/31*** | (2006.01) |
| ***A61M 5/50*** | (2006.01) |

(52) U.S. Cl.

CPC .............. *A61K 9/08* (2013.01); *A61K 9/0019* (2013.01); *A61K 31/135* (2013.01); *A61K 47/02* (2013.01); *A61K 47/22* (2013.01); *A61M 5/3129* (2013.01); *A61M 5/5086* (2013.01)

(58) Field of Classification Search

CPC ...... A61K 9/08; A61K 9/0019; A61K 31/135; A61K 47/02; A61K 47/22; A61M 5/3129; A61M 5/5086

See application file for complete search history.

(56) References Cited

U.S. PATENT DOCUMENTS

| | | | | |
|---|---|---|---|---|
| 5,783,269 | A | 7/1998 | Heilmann et al. | |
| 7,828,787 | B2 | 11/2010 | Brandenburger et al. | |
| 7,875,016 | B2 | 1/2011 | Pahlberg et al. | |
| 8,118,802 | B2 | 2/2012 | Brandenburger et al. | |
| 8,162,915 | B2 | 4/2012 | Brandenburger et al. | |
| 10,214,338 | B2 | 2/2019 | Devouassoux et al. | |
| 10,661,030 | B1 | 5/2020 | Murray et al. | |
| 11,305,072 | B2 | 4/2022 | Murray et al. | |
| 11,883,364 | B2 | 1/2024 | Brandenburger | |
| 11,964,142 | B2 | 4/2024 | Murray et al. | |
| 12,005,026 | B2 | 6/2024 | Brandenburger et al. | |
| 12,171,992 | B2 | 12/2024 | Murray et al. | |
| 12,390,397 | B2 | 8/2025 | Brandenburger et al. | |
| 12,403,262 | B2 | 9/2025 | Murray et al. | |
| 2014/0275276 | A1* | 9/2014 | Basstanie ................. | A61K 9/08 514/646 |
| 2015/0273133 | A1 | 10/2015 | Kerschbaumer et al. | |
| 2022/0160655 | A1 | 5/2022 | Weg | |
| 2023/0310749 | A1* | 10/2023 | Jarmusik ................ | A61K 47/02 604/111 |
| 2025/0025431 | A1 | 1/2025 | Dusci | |
| 2025/0127900 | A1 | 4/2025 | Jain et al. | |
| 2025/0205160 | A1 | 6/2025 | Agnihotri et al. | |
| 2025/0255834 | A1 | 8/2025 | Weg | |
| 2025/0312294 | A1 | 10/2025 | Dusci | |

FOREIGN PATENT DOCUMENTS

| | | | |
|---|---|---|---|
| CN | 109172550 | A | 1/2019 |
| WO | 2023119100 | A1 | 6/2023 |
| WO | 2024062443 | A1 | 3/2024 |
| WO | 2024127365 | A1 | 6/2024 |
| WO | 2024171074 | A1 | 8/2024 |
| WO | 2024254522 | A2 | 12/2024 |

OTHER PUBLICATIONS

Fresenius Kabi Ketamine Hydrochloride Injection formulations; “Pharmacompass”; (www.pharmacompass.com/ndc-65219-184-01); six page pdf of formulations on sale as of Jul. 10, 2023. “On-sale” publication date of Jul. 10, 2023.*

Licht et al., Carcinogenesis; vol. 9, No. 3, pp. 365-372. Published 1988.*

Yuan et al.; J. Agric. Food Chem.; 46, pp. 5078-5082. Published Nov. 21, 1998.*

Tannenbaum et al.; Annals of New York Academy of Sciences; pp. 354-363. Published 1987.*

Toyama et al.; Environmental Health and Preventive Medicine; 11, pp. 120-127. Published May 2006.*

Homšak et al., “Assessment of a Diverse Array of Nitrite Scavengers in Solutions and Solid State: A Study of Inhibitory Effect on the Formation of Alkyl-Aryl and Dialkyl N-Nitrosamine Derivatives,” Processes 10(11): 2428 (2022) 18 pages XP093014011, CH, ISSN: 2227-9717, DOI: 10.3390/pr10112428.

European Patent Office, International Search Report in International Application No. PCT/US2025/054413 (Mar. 10, 2026).

European Patent Office, Written Opinion in International Application No. PCT/US2005/054413 (Mar. 10, 2026).

“Ketalar—ketamine hydrochloride injection,” Highlights of prescribing information Jun. 2025, Par Health USA, LLC, Rochester, MI, USA (20 pgs.).

Bayne et al., “N-nitrosamine Mitigation with Nitrite Scavengers in Oral Pharmaceutical Drug Products,” Journal of Pharmaceutical Sciences 112: 1794-1800 (2023).

(Continued)

*Primary Examiner* — Jeffrey T. Palenik

(74) *Attorney, Agent, or Firm* — Leydig, Voit & Mayer, Ltd.

(57) ABSTRACT

The invention provides a sterile, injectable pharmaceutical composition which includes a therapeutically effective amount of ketamine or a pharmaceutically acceptable salt thereof, a nitrite scavenger, a tonicity agent, and water, wherein the composition contains less than about 300 ppb of an N-nitrosoketamine impurity. The invention also provides a pharmaceutical product which includes a container and the composition of the invention aseptically sealed therein. The invention further provides a process for preparing the composition and product of the invention.

18 Claims, No Drawings

(56) References Cited

OTHER PUBLICATIONS

Moretti et al., "A single coadministration of subeffective doses of ascorbic acid and ketamine reverses the depressive-like behavior induced by chronic unpredictable stress in mice," Pharmacology, Biochemistry and Behavior 187: 172800 (2019) (8 pgs.).

Schlingemann et al., "The Landscape of Potential Small and Drug Substance Related Nitrosamines in Pharmaceuticals," Journal of Pharmaceutical Sciences 112: 1287-1304 (2023).

* cited by examiner

KETAMINE FORMULATION

CROSS REFERENCE TO RELATED PATENT APPLICATION(S)

This patent application claims the benefit of U.S. Patent Application No. 63/717,086 filed on Nov. 6, 2024, which is incorporated by reference herein in its entirety.

BACKGROUND OF THE INVENTION

Ketamine is an N-methyl-D-aspartate (NMDA) receptor antagonist used medically as a dissociative anesthetic for the induction and maintenance of anesthesia before and during medical procedures, e.g., surgery and diagnostic, which involve anesthesia. An injectable form of ketamine was approved in the United States in 1970 under the brand name Ketalar®, which is formulated a sterile solution containing a racemic mixture of ketamine hydrochloride, also referred to as dl 2-(o-chlorophenyl)-2(methylamino) cyclohexanone hydrochloride. Ketamine hydrochloride has the following molecular formula:

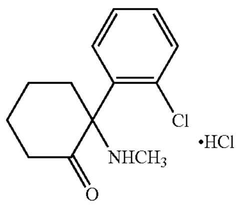

Ketamine Hydrochloride

Ketalar® is a rapid-acting general anesthetic for producing an anesthetic state characterized by profound analgesia, normal pharyngeal-laryngeal reflexes, normal or slightly enhanced skeletal muscle tone, and cardiovascular and respiratory stimulation, with occasional transient and minimal respiratory depression. The mechanism of action for anesthesia is primarily due to antagonism of NMDA receptors in the central nervous system.

Ketalar® is formulated as a slightly acidic (pH 3.5-5.5), sterile, aqueous solution for intravenous or intramuscular injection containing ketamine hydrochloride at concentrations equivalent to either 10 mg/mL, 50 mg/mL, or 100 mg/mL of ketamine base, and not more than 0.1 mg/mL Phemerol® (benzethonium chloride) added as a preservative. The 10 mg/mL solution of Ketalar® is made isotonic with sodium chloride. For the 50 mg/mL and 100 mg/mL solutions of Ketalar®, dilution with Sterile Water for injection, USP, 0.9% Sodium Chloride Injection, USP (Normal Saline), or 5% Dextrose Injection, USP is recommended prior to intravenous injection.

There remains a need in the art for an improved injectable formulation of ketamine that is storage stable and has reduced impurity levels during storage, preferably for longer durations at room temperature.

BRIEF SUMMARY OF THE INVENTION

The invention provides a sterile, injectable pharmaceutical composition which includes a therapeutically effective amount of ketamine or a pharmaceutically acceptable salt thereof, a nitrite scavenger, a tonicity agent, and water, wherein the composition contains less than about 1500 ppb (parts per billion) of an N-nitrosoketamine (NNK) impurity after manufacture and/or throughout a storage period. The composition of the invention may be administered by injection, e.g., intravenously or intramuscularly, to produce and/or maintain anesthesia, e.g., in a human patient, in a manner similar to which Ketalar® is administered for its approved indications and uses.

The invention also provides a pharmaceutical product which includes a container and the composition of the invention aseptically sealed in the container. The container may include, for example, any suitable vial, bottle, bag, or syringe which is used in the pharmaceutical industry for storing an injectable dosage form of a drug.

The invention further provides a process for preparing the composition of the invention as described herein, which method generally includes:

- dissolving a tonicity agent in water,
- dissolving a nitrite scavenger in the water, and
- dissolving ketamine or a pharmaceutically acceptable salt thereof in the water.

In some embodiments, the process of the invention includes, for example:

- dissolving sodium chloride in water in an amount sufficient to achieve a final concentration of from about 6 mg/mL to about 7 mg/mL sodium chloride in the composition,
- dissolving ascorbic acid in the water in an amount sufficient to achieve a final concentration of from about 0.1 μg/mL to about 10 mg/mL ascorbic acid in the composition, and
- dissolving ketamine hydrochloride in the water in an amount sufficient to achieve a final concentration equivalent to about 10 mg/mL of ketamine free base in the composition,
- wherein the final concentration of ascorbic acid achieved in the composition includes any exemplary concentrations and ranges of concentrations of ascorbic as described herein, e.g., from about 0.002 mg/mL to about 1.0 mg/mL ascorbic acid.

The composition produced by the inventive process may be aseptically filled into any suitable container(s) as described herein, and the filled container(s) may be sealed to provide a pharmaceutical product as described herein.

DETAILED DESCRIPTION OF THE INVENTION

The invention is predicated, at least in part, on the surprising and unexpected discovery that certain nitrite scavengers such as, for example, an antioxidant, e.g., ascorbic acid, can substantially reduce the content of NNK impurities in a sterile, injectable aqueous ketamine formulation under long-term storage conditions without adversely impacting the stability of ketamine in the formulation. The invention thus provides a sterile, injectable pharmaceutical composition which includes a therapeutically effective amount of ketamine or a pharmaceutically acceptable salt thereof, a nitrite scavenger, a tonicity agent, and water, wherein the composition contains less than about 1500 ppb, e.g., less than about 1400 ppb, less than about 1250 ppb, less than about 1000 ppb, less than about 750 ppb, less than about 500 ppb, less than about 400 ppb, less than about 300 ppb, less than about 250 ppb, less than about 200 ppb, less than about 150 ppb, less than about 100 ppb, less than about 75 ppb, less than about 50 ppb, less than about 40 ppb, or less than about 30 ppb, of an NNK impurity. In certain embodiments, the composition of the invention contains about 25 ppb to about 1500 ppb, e.g., about 30 ppb to about 300 ppb, about 35 ppb to about 250 ppb, about 40 ppb to about 200 ppb, about 150 ppb to about 300 ppb, about 200 ppb to about 400 ppb, about 100 ppb to about 500 ppb, or about 100 ppb to about 250 ppb, of an NNK impurity.

The composition of the invention minimizes NNK impurity levels during storage under room temperature conditions (e.g., 25° C.±2° C./40% relative humidity (RH)±5% RH or 25° C.±2° C./60% RH±5% RH). In some embodiments, the composition of the invention contains less than about 1500 ppb, e.g., less than about 1400 ppb, less than about 1250 ppb, less than about 1000 ppb, less than about 750 ppb, less than about 500 ppb, less than about 400 ppb, less than about 300 ppb, less than about 250 ppb, less than about 200 ppb, less than about 150 ppb, less than about 100 ppb, less than about 75 ppb, or less than about 50 ppb of an NNK impurity after storage under room temperature conditions for 3 months, 6 months, 9 months, 12 months, 18 months, or 24 months. In certain embodiments, the composition of the invention contains about 50 ppb to about 1500 ppb, e.g., about 50 ppb to about 400 ppb, about 75 ppb to about 350 ppb, about 100 ppb to about 350 ppb, about 150 ppb to about 300 ppb, about 200 ppb to about 400 ppb, about 100 ppb to about 500 ppb, or about 100 ppb to about 250 ppb, of an NNK impurity after storage under room temperature conditions for 3 months, 6 months, 9 months, 12 months, 18 months, or 24 months.

The composition of the invention also minimizes NNK impurity levels during storage above 25° C., e.g., under intermediate storage conditions (e.g., at 30° C.±2° C./65% RH±5% RH) or accelerated storage conditions (e.g., at 40° C.±2° C./75% RH±5% RH or 40° C.±2° C./not more than 25% RH). For example, in some embodiments, the composition of the invention contains less than about 2000 ppb, e.g., less than about 1750 ppb, less than about 1500 ppb, less than about 1000 ppb, less than about 750 ppb, less than about 500 ppb, less than about 400 ppb, less than about 300 ppb, less than about 250 ppb, less than about 200 ppb, less than about 150 ppb, or less than about 100 ppb of an NNK impurity after storage under intermediate or accelerated storage conditions for 1 month, 2 months, 3 months, 6 months, 9 months, or 12 months. In other embodiments, the composition of the invention contains about 100 ppb to about 2000 ppb, e.g., about 150 ppb to about 1500 ppb, about 200 ppb to about 800 ppb, about 250 ppb to about 750 ppb, about 150 ppb to about 300 ppb, about 200 ppb to about 400 ppb, about 100 ppb to about 500 ppb, or about 100 ppb to about 250 ppb, of an NNK impurity after storage under intermediate or accelerated storage conditions for 1 month, 2 months, 3 months, 6 months, 9 months, or 12 months.

Any suitable form of ketamine or pharmaceutically acceptable salt thereof may be included in the composition of the invention. Suitable forms of ketamine include, for example, pharmaceutically acceptable acid addition salts, e.g., ketamine hydrochloride. In some embodiments, the ketamine used in formulating the composition is ketamine hydrochloride.

The therapeutically effective amount of ketamine or pharmaceutically acceptable salt thereof preferably includes an amount of ketamine free base equivalent sufficient to provide anesthesia in a human patient when delivered via intravenous or intramuscular injection. Preferably, the therapeutically effective amount of ketamine or pharmaceutically acceptable salt thereof is sufficient to provide rapid anesthesia in a human patient for diagnostic and surgical procedures that do not require skeletal muscle relaxation. In some embodiments, the ketamine or pharmaceutically acceptable salt thereof is present in the composition at a concentration equivalent to about 0.1 mg/mL to about 100 mg/mL, e.g., about 0.5 mg/mL to about 50 mg/mL about 1 mg/mL to about 50 mg/mL, about 0.5 mg/mL to about 20 mg/mL, about 1 mg/mL to about 20 mg/mL, about 1 mg/mL to about 10 mg/mL, about 2 mg/mL to about 15 mg/mL, about 8 mg/mL to about 12 mg/mL, or about 1 mg/mL to about 2 mg/mL, of the free base. In some embodiments, the ketamine or pharmaceutically acceptable salt thereof is present in the composition at a concentration equivalent to about 10 mg/mL of the free base, which is preferably packaged in dosages sufficient to provide rapid onset of anesthesia in a human patient. In other embodiments, the ketamine or pharmaceutically acceptable salt thereof is present in the composition at a concentration equivalent to about 1 mg/mL, about 2 mg/mL, or about 5 mg/mL of the free base. In some embodiments, the ketamine or pharmaceutically acceptable salt thereof is present in the composition at a concentration equivalent to about 10 mg/mL of the free base and is provided in a 1-5 mL dosage form contained, e.g., in a vial or pre-filled syringe. In other embodiments, the ketamine or pharmaceutically acceptable salt thereof is present in the composition at a concentration equivalent to about 1 mg/mL to about 2 mg/mL of the free base and is provided in a 50-200 mL dosage form contained, e.g., in a bag or bottle.

The nitrite scavenger used in the composition of the invention may include any water soluble nitrite scavenger which is capable of maintaining NNK impurity levels below about 1500 ppb without adversely impacting the stability of the ketamine in the composition, e.g., such that at least about 90-95% of the original ketamine content is retained during storage. In some embodiments, the nitrite scavenger used in the composition of the invention is capable of maintaining NNK impurity levels below about 1500 ppb, e.g., below about 1000 ppb, below about 750 ppb, below about 500 ppb, or below about 250 ppb after 3-24 months of storage at under room temperature conditions without adversely impacting the stability of the ketamine in the composition, e.g., such that at least about 90-95% of the original ketamine content is retained during storage. Preferably, the nitrite scavenger used in the composition of the invention is capable of maintaining NNK impurity levels below about 300 ppb after 3-6 months of storage under room temperature conditions, e.g., after 6 months of storage at about 25° C., without adversely impacting the stability of the ketamine in the composition, e.g., such that at least about 90-95% of the original ketamine content is retained during storage.

In some embodiments, the nitrite scavenger used in the composition of the invention is an antioxidant such as, for example, ascorbic acid or a pharmaceutically acceptable salt thereof (e.g., sodium ascorbate). In certain embodiments, the nitrite scavenger used in the composition of the invention is ascorbic acid. In other embodiments, the nitrite scavenger may include, e.g., glycine, cysteine, lysine, histidine, arginine, ferulic acid, caffeic acid, a tocopherol (e.g., alpha tocopherol), combinations thereof, and pharmaceutically acceptable salts or derivatives (e.g., esters) thereof.

When the nitrite scavenger is ascorbic acid (or a pharmaceutically acceptable salt thereof), the composition of the invention preferably includes ascorbic acid at a concentration ranging from about 0.1 μg/mL to about 10 mg/mL, about 0.5 μg/mL to about 2.0 mg/mL, or about 0.001 mg/mL to about 1.0 mg/mL. In some embodiments, the composition of the invention contains ascorbic acid at a concentration of from about 0.002 mg/mL to about 0.5 mg/mL. In other embodiments, the composition of the invention contains from about 0.05 mg/mL to about 0.5 mg/mL ascorbic acid. In other embodiments, the composition of the invention contains from about 0.05 mg/mL to about 0.2 mg/mL ascorbic acid, e.g., from about 0.05 mg/mL to about 0.1 mg/mL ascorbic acid, or from about 0.1 mg/mL to about 0.2 mg/mL ascorbic acid. In certain embodiments, the composition of the invention contains about 0.1 μg/mL ascorbic acid, about 0.5 μg/mL ascorbic acid, about 0.001 mg/mL ascorbic acid, about 0.005 mg/mL ascorbic acid, about 0.01 mg/mL ascorbic acid, about 0.02 mg/mL ascorbic acid, about 0.025 mg/mL ascorbic acid, about 0.03 mg/mL ascorbic acid, about 0.04 mg/mL ascorbic acid, about 0.05 mg/mL ascorbic acid, about 0.1 mg/mL ascorbic acid, about 0.2 mg/mL ascorbic acid, about 0.5 mg/mL ascorbic acid, or about 1.0 mg/mL ascorbic acid.

Any suitable tonicity agent may be used in the composition of the invention. Suitable tonicity agents may include one or more tonicity agents commonly used in injectable formulations. Such tonicity agents may include, for example, dextrose, glycerin, mannitol, potassium chloride, sodium chloride, and the like, and combinations thereof. In some embodiments, the tonicity agent used in the composition of the invention is sodium chloride. The tonicity agent may be present in an amount that renders the composition isotonic. For example, the tonicity agent may present in an amount sufficient to provide the composition with an osmolality of about 250-350 mOsm/kg, e.g., about 250-310 mOsm/kg, about 270-330 mOsm/kg, about 260-320 mOsm/kg, about 300-340 mOsm/kg, or about 310-330 mOsm/kg. In some embodiments, the tonicity agent is present in an amount that provides the composition with an osmolality of 290 mOsm/kg±10%. When sodium chloride is used as the tonicity agent, the composition of the invention preferably includes from about 4 mg/mL to about 9 mg/mL, e.g., about 6 mg/mL to about 7 mg/mL sodium chloride.

In some embodiments, the composition of the invention includes a sterile, injectable pharmaceutical composition containing ketamine hydrochloride at a concentration equivalent to about 10 mg/mL of the free base, from about 0.002 mg/mL to about 1.0 mg/mL of ascorbic acid, from about 6 mg/mL to about 7 mg/mL sodium chloride, and water. The composition of the invention also includes, for example, a sterile, injectable pharmaceutical composition containing ketamine hydrochloride at a concentration equivalent to about 10 mg/mL of the free base, from about 0.005 mg/mL to about 0.1 mg/mL of ascorbic acid, from about 6 mg/mL to about 7 mg/mL sodium chloride, and water. The composition of the invention further includes, for example, a sterile, injectable pharmaceutical composition containing ketamine hydrochloride at a concentration equivalent to about 10 mg/mL of the free base, from about 0.01 mg/mL to about 0.05 mg/mL of ascorbic acid (e.g., from about 0.02 mg/mL to about 0.04 mg/mL ascorbic acid, or from about 0.025 mg/mL to about 0.035 mg/mL ascorbic acid), from about 6 mg/mL to about 7 mg/mL sodium chloride, and water.

The composition of the invention thus may include, for example, a sterile, injectable pharmaceutical composition containing ketamine hydrochloride at a concentration equivalent to about 10 mg/mL of the free base, about 0.01 mg/mL of ascorbic acid, from about 6 mg/mL to about 7 mg/mL sodium chloride, and water. The composition of the invention also may include, for example, a sterile, injectable pharmaceutical composition containing ketamine hydrochloride at a concentration equivalent to about 10 mg/mL of the free base, about 0.025 mg/mL of ascorbic acid, from about 6 mg/mL to about 7 mg/mL sodium chloride, and water. The composition of the invention additionally may include, for example, a sterile, injectable pharmaceutical composition containing ketamine hydrochloride at a concentration equivalent to about 10 mg/mL of the free base, about 0.05 mg/mL of ascorbic acid, from about 6 mg/mL to about 7 mg/mL sodium chloride, and water. The composition of the invention further may include, for example, a sterile, injectable pharmaceutical composition containing ketamine hydrochloride at a concentration equivalent to about 10 mg/mL of the free base, about 0.1 mg/mL of ascorbic acid, from about 6 mg/mL to about 7 mg/mL sodium chloride, and water. The composition of the invention additionally may include, for example, a sterile, injectable pharmaceutical composition containing ketamine hydrochloride at a concentration equivalent to about 10 mg/mL of the free base, about 0.2 mg/mL of ascorbic acid, from about 6 mg/mL to about 7 mg/mL sodium chloride, and water. The composition of the invention further may include, for example, a sterile, injectable pharmaceutical composition containing ketamine hydrochloride at a concentration equivalent to about 10 mg/mL of the free base, about 0.5 mg/mL of ascorbic acid, from about 6 mg/mL to about 7 mg/mL sodium chloride, and water.

In some embodiments, the composition of the invention has a pH of about 3.5 to about 5.5, e.g., about 4.0 to about 5.0, about 4.2 to about 4.8, about 4.3 to about 4.7, or about 4.5 to about 4.6, e.g., when initially filled into a container such as, e.g., a vial, bottle, bag, or syringe suitable for long term storage.

The composition of the invention may comprise a pH adjuster (in addition to the nitrite scavenger, which may impact pH). The pH adjuster may include any suitable acid and/or base. A suitable pH adjuster may include, for example, hydrochloric acid (HCl), sodium hydroxide (NaOH), potassium hydroxide or a combination thereof. In some embodiments, the pH adjuster includes HCl and/or NaOH.

The composition of the invention may comprise at least one buffer component (in addition to the nitrite scavenger which may have buffering capacity depending upon, e.g., concentration, presence of conjugate base or acid, and/or pH). In some embodiments, however, the composition is free of a buffer component, or substantially free of a buffer component. If present, the type and amount of buffer component present in the composition may be selected based on several considerations, including but not limited to, for example, a target pH, pH stabilization, impurity formation, coloration, and/or patient tolerance upon administration. In some embodiments, the composition includes a weak acid and a conjugate base of the weak acid. The weak acid and conjugate base may be added to the composition in an anhydrous or hydrated form. In some embodiments, the conjugate base may be present in salt form. The invention also includes embodiments in which the acid or weak acid component may be a dicarboxylic acid or a tricarboxylic acid. For example, the acid may include citric acid, isocitric acid, aconitic acid, trimesic acid, propane-1,2,3-tricarboxylic acid, fumaric acid, oxalic acid, maleic acid, malonic acid, glutaric acid, succinic acid, tartaric acid, or a combination thereof. In some embodiments, the buffer includes citric acid and a salt thereof (i.e., a citrate salt).

In certain embodiments, the composition of the invention may include a sterile, injectable pharmaceutical composition containing ketamine hydrochloride at a concentration equivalent to about 10 mg/mL of the free base, from about 0.005 mg/mL to about 1.0 mg/mL of ascorbic acid, from about 6 mg/mL to about 7 mg/mL sodium chloride, and water, wherein the pH is about 4.5-4.6, e.g., when initially filled into a suitable container for storage. The composition of the invention also may include a sterile, injectable pharmaceutical composition containing ketamine hydrochloride at a concentration equivalent to about 10 mg/mL of the free base, from about 0.005 mg/mL to about 0.5 mg/mL of ascorbic acid, from about 6 mg/mL to about 7 mg/mL sodium chloride, and water, wherein the pH is about 4.5-4.6, e.g., when initially filled into a suitable container for storage. The composition of the invention further may include a sterile, injectable pharmaceutical composition containing ketamine hydrochloride at a concentration equivalent to about 10 mg/mL of the free base, from about 0.05 mg/mL to about 0.2 mg/mL of ascorbic acid, from about 6 mg/mL to about 7 mg/mL sodium chloride, and water, wherein the pH is about 4.5-4.6, e.g., when initially filled into a suitable container for storage.

The composition of the invention thus may include, for example, a sterile, injectable pharmaceutical composition containing ketamine hydrochloride at a concentration equivalent to about 10 mg/mL of the free base, about 0.005 mg/mL of ascorbic acid, from about 6 mg/mL to about 7 mg/mL sodium chloride, and water, wherein the pH is about 4.5-4.6, e.g., when initially filled into a suitable container for storage. The composition of the invention also may include, for example, a sterile, injectable pharmaceutical composition containing ketamine hydrochloride at a concentration equivalent to about 10 mg/mL of the free base, about 0.05 mg/mL of ascorbic acid, from about 6 mg/mL to about 7 mg/mL sodium chloride, and water, wherein the pH is about 4.5-4.6, e.g., when initially filled into a suitable container for storage. The composition of the invention additionally may include, for example, a sterile, injectable pharmaceutical composition containing ketamine hydrochloride at a concentration equivalent to about 10 mg/mL of the free base, about 0.1 mg/mL of ascorbic acid, from about 6 mg/mL to about 7 mg/mL sodium chloride, and water, wherein the pH is about 4.5-4.6, e.g., when initially filled into a suitable container for storage. The composition of the invention further may include, for example, a sterile, injectable pharmaceutical composition containing ketamine hydrochloride at a concentration equivalent to about 10 mg/mL of the free base, about 0.2 mg/mL of ascorbic acid, from about 6 mg/mL to about 7 mg/mL sodium chloride, and water, wherein the pH is about 4.5-4.6, e.g., when initially filled into a suitable container for storage. The composition of the invention additionally may include, for example, a sterile, injectable pharmaceutical composition containing ketamine hydrochloride at a concentration equivalent to about 10 mg/mL of the free base, about 0.5 mg/mL of ascorbic acid, from about 6 mg/mL to about 7 mg/mL sodium chloride, and water, wherein the pH is about 4.5-4.6, e.g., when initially filled into a suitable container for storage. The composition of the invention further may include, for example, a sterile, injectable pharmaceutical composition containing ketamine hydrochloride at a concentration equivalent to about 10 mg/mL of the free base, about 1.0 mg/mL of ascorbic acid, from about 6 mg/mL to about 7 mg/mL sodium chloride, and water, wherein the pH is about 4.5-4.6, e.g., when initially filled into a suitable container for storage.

The composition of the invention is stable. As used herein, the terms "stable" and "stability" refer to any characteristic of the composition which may change or be affected by storage conditions including, without limitation, potency, nitrosamine (e.g., NNK) content, total impurities, ketamine degradation products, specific optical rotation, optical purity, appearance, viscosity, sterility, particulates (visible and subvisible), color, and/or clarity. The storage conditions which may affect stability may include, for example, duration, temperature, humidity, and/or light exposure.

For example, a stable ketamine composition may refer to a composition that contains at least about 90%, e.g., at least about 95%, at least about 96%, at least about 97%, at least about 98%, at least about 99%, or at least about 99.5% of the labeled concentration of ketamine or pharmaceutically acceptable salt thereof after storage under room temperature (e.g., 25° C.±2° C./60% RH±5% RH or 25° C.±2° C./40% RH±5% RH), intermediate (e.g., at 30° C.±2° C./65% RH±5% RH), and/or accelerated (e.g., at 40° C.±2° C./75% RH±5% RH or 40° C.±2° C./not more than 25% RH) conditions for 1-24 months, e.g., 1 month, 2 months, 3 months, 6 months, 9 months, 12 months, 18 months, or 24 months. A stable ketamine composition also may refer to a composition that remains therapeutically effective and contains less than about 110%, e.g., less than about 95%, less than about 104%, less than about 103%, less than about 102%, less than about 101%, or less than about 100.5%, of the of the labeled concentration of ketamine or pharmaceutically acceptable salt thereof after storage under room temperature, intermediate, and/or accelerated conditions for 1-24 months, e.g., 1 month, 2 months, 3 months, 6 months, 9 months, 12 months, 18 months, or 24 months. A stable ketamine composition additionally may refer to a composition that contains an amount of ketamine bounded by any two of the foregoing endpoints. For example, a stable ketamine composition may contain from about 90% to about 110%, from about 95% to about 105%, from about 97% to about 103%, from about 98% to about 102%, or from about 99% to about 101%, of the labeled concentration of ketamine or pharmaceutically acceptable salt thereof after storage under room temperature, intermediate, and/or accelerated conditions for 1-24 months, e.g., 1 month, 2 months, 3 months, 6 months, 9 months, 12 months, 18 months, or 24 months.

A stable ketamine composition also may refer to a composition that contains less than about 5.0% (area percent), e.g., less than about 4.0%, less than about 3.0%, less than about 2.5%, less than about 2.0%, less than about 1.5%, less than about 1.0%, less than about 0.9%, less than about 0.8%, less than about 0.7%, less than about 0.6%, or less than about 0.5%, of total ketamine-related impurities present in the composition after storage under room temperature, intermediate, and/or accelerated conditions for 1-24 months, e.g., 1 month, 2 months, 3 months, 6 months, 9 months, 12 months, 18 months, or 24 months. A stable ketamine composition additionally may refer to a composition that remains safe and effective and contains total ketamine-related impurities present in an amount of about 0.1% or more, e.g., about 0.2% or more, about 0.3% or more, about 0.4% or more, about 0.5% or more, about 0.6% or more, about 0.7% or more, about 0.8% or more, about 1.0% or more, about 1.5% or more, about 2.0% or more, or about 2.5% or more, after storage under room temperature, intermediate, and/or accelerated conditions for 1-24 months, e.g., 1 month, 2 months, 3 months, 6 months, 9 months, 12 months, 18 months, or 24 months. A stable ketamine composition also may refer to a composition that contains total ketamine-related impurities present in an amount bounded by any two of the aforementioned endpoints. For example, a stable ketamine composition also may refer to a composition that contains from about 0.1% to about 5.0%, e.g., from about 0.2% to about 4.0%, from about 0.2% to about 3.0%, from about 0.2% to about 2.0%, from about 0.2% to about 1.5%, from about 0.1% to about 1.0%, from about 0.1% to about 0.7%, from about 0.2% to about 0.7%, from about 0.3% to about 0.7%, or from about 0.4% to about 0.7%, of total ketamine-related impurities present in the composition after storage under room temperature, intermediate, and/or accelerated conditions for 1-24 months, e.g., 1 month, 2 months, 3 months, 6 months, 9 months, 12 months, 18 months, or 24 months.

A stable ketamine composition also may refer to a composition that contains less than about 2.0% (area percent), e.g., less than about 1.5%, less than about 1.0%, less than about 0.8%, less than about 0.4%, less than about 0.3%, less than about 0.25%, less than about 0.2%, less than about 0.15%, less than about 0.1%, or less than about 0.05%, of any individual ketamine-related impurity present in the composition after storage under room temperature, intermediate, and/or accelerated conditions for 1-24 months, e.g., 1 month, 2 months, 3 months, 6 months, 9 months, 12 months, 18 months, or 24 months. A stable ketamine composition additionally may refer to a composition that remains safe and effective and contains any individual ketamine-related impurity present in an amount of about 0.02% or more, e.g., about 0.05% or more, about 0.08% or more, about 0.1% or more, about 0.12% or more, about 0.15% or more, about 0.18% or more, about 0.2% or more, or about 0.3% or more, after storage under room temperature, intermediate, and/or accelerated conditions for 1-24 months, e.g., 1 month, 2 months, 3 months, 6 months, 9 months, 12 months, 18 months, or 24 months. A stable ketamine composition also may refer to a composition that contains any individual ketamine-related impurity present in an amount bounded by any two of the aforementioned endpoints. For example, a stable ketamine composition additionally may refer to a composition that contains from about 0.02% to about 2.0%, from about 0.05% to about 1.0%, from about 0.08% to about 0.8%, from about 0.08% to about 0.400, from about 0.0800 to about 0.20%, from about 0.1 to about 0.20%, or from about 0.05% to about 0.25% of any individual ketamine-related impurity present in the composition after storage under room temperature, intermediate, and/or accelerated conditions for 1-24 months, e.g., 1 month, 2 months, 3 months, 6 months, 9 months, 12 months, 18 months, or 24 months.

In some embodiments, an individual ketamine-related impurity may refer to a ketamine degradation product and/or starting material, reactant, and/or intermediate of a synthetic process for making ketamine or a pharmaceutically acceptable salt thereof. For example, an individual ketamine-related impurity may include, but are not limited to, Related Compound A, Impurity B, and Impurity C, as described herein (e.g., Table 1) as well as any individual unknown impurity.

TABLE 1

Ketamine Related Impurities

| Name | Structure, Formula and Molecular Weight |
| --- | --- |
| Related Compound A (1-[(2 chlorophenyl) (methylimino) methyl]cyclopentanol) | 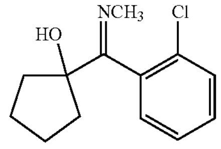 $C_{12}H_{16}ClNO$ 237.73 g/mol |

TABLE 1-continued

Ketamine Related Impurities

| Name | Structure, Formula and Molecular Weight |
| --- | --- |
| Impurity B (2-(2-Chlorophenyl)-2-hydroxycyclohexanone) | 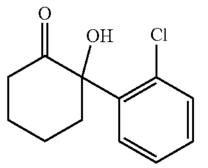 [SMILES: O=C1CCCCC1(O)c1ccccc1Cl] $C_{12}H_{13}ClO_2$ 224.68 g/mol |
| Impurity C ((2-Chlorophenyl) (1-hydroxycyclopentyl) methanone) | 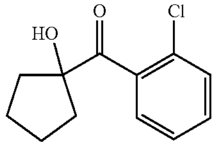 [SMILES: O=C(c1ccccc1Cl)C1(O)CCCC1] $C_{12}H_{13}ClO_2$ 224.69 g/mol |

In some embodiments, a stable ketamine composition refers to a composition that comprises one or more of Related Compound A, Impurity B, Impurity C, or any individual unknown impurity after manufacture and/or storage under room temperature, intermediate, and/or accelerated conditions. For example, a stable ketamine composition may comprise each of Related Compound A, Impurity B, Impurity C, and/or any individual unknown impurity in an amount less than about 2.0% (area percent), e.g., less than about 1.5%, less than about 1.0%, less than about 0.8%, less than about 0.4%, less than about 0.3%, less than about 0.25%, less than about 0.2%, less than about 0.15%, less than about 0.1%, or less than about 0.05%, of any individual ketamine-related impurity present in the composition after storage under room temperature, intermediate, and/or accelerated conditions for 1-24 months, e.g., 1 month, 2 months, 3 months, 6 months, 9 months, 12 months, 18 months, or 24 months. A stable ketamine composition additionally may refer to a composition that remains safe and effective and contains each of Related Compound A, Impurity B, Impurity C, and/or any individual unknown impurity present in an amount of about 0.02% or more, e.g., about 0.05% or more, about 0.08% or more, about 0.1% or more, about 0.12% or more, about 0.15% or more, about 0.18% or more, about 0.2% or more, or about 0.3% or more, after storage under room temperature, intermediate, and/or accelerated conditions for 1-24 months, e.g., 1 month, 2 months, 3 months, 6 months, 9 months, 12 months, 18 months, or 24 months. A stable ketamine composition also may refer to a composition that contains each of Related Compound A, Impurity B, Impurity C, and/or any individual unknown impurity present in an amount bounded by any two of the aforementioned endpoints. For example, a stable ketamine composition additionally may refer to a composition that contains from about 0.02% to about 2.0%, from about 0.05% to about 1.0%, from about 0.08% to about 0.8%, from about 0.08% to about 0.4%, from about 0.08% to about 0.2%, from about 0.1 to about 0.2%, or from about 0.05% to about 0.25% of each of Related Compound A, Impurity B, Impurity C, and/or any individual unknown impurity present in the composition after storage under room temperature, intermediate, and/or accelerated conditions for 1-24 months, e.g., 1 month, 2 months, 3 months, 6 months, 9 months, 12 months, 18 months, or 24 months.

In certain embodiments, a stable ketamine composition refers to a composition that comprises minimal amounts of the ascorbic acid degradation product, furfural, after manufacture and/or storage under room temperature, intermediate, and/or accelerated conditions. For example, a stable ketamine composition may contain furfural in an amount less than about 20% by weight of ascorbic acid, e.g., less than about 15%, less than about 10%, less than about 8%, less than about 4%, less than about 2%, less than about 1.5%, less than about 1.0%, less than about 0.5%, less than about 0.1%, less than about 0.05%, or less than about 0.01%, w/w of ascorbic acid after storage under room temperature, intermediate, and/or accelerated conditions for 1-24 months, e.g., 1 month, 2 months, 3 months, 6 months, 9 months, 12 months, 18 months, or 24 months. A stable ketamine composition additionally may refer to a composition that remains safe and effective and contains furfural present in an amount of about 0.001% or more, e.g., about 0.005% or more, about 0.01% or more, about 0.05% or more, about 0.1% or more, about 0.2% or more, about 0.5% or more, about 1.0% or more, or about 2.0% or more, w/w of ascorbic acid, after storage under room temperature, intermediate, and/or accelerated conditions for 1-24 months, e.g., 1 month, 2 months, 3 months, 6 months, 9 months, 12 months, 18 months, or 24 months. A stable ketamine composition also may refer to a composition that contains furfural present in an amount bounded by any two of the aforementioned endpoints. For example, a stable ketamine composition additionally may refer to a composition that contains from about 0.001% to about 20%, from about 0.01% to about 2.0%, from about 0.05% to about 1.0%, from about 0.05% to about 0.5%, from about 0.1% to about 10%, from about 0.2 to about 4%, or from about 0.5% to about 5% of furfural w/w of ascorbic acid after storage under room temperature, intermediate, and/or accelerated conditions for 1-24 months, e.g., 1 month, 2 months, 3 months, 6 months, 9 months, 12 months, 18 months, or 24 months.

In other embodiments, a stable ketamine composition comprises less than about 100 μg/mL furfural (w/v), e.g., less than about 50 μg/mL, less than about 25 μg/mL, less than about 10 μg/mL, less than about 5 μg/mL, less than about 2 μg/mL, less than about 1.5 μg/mL, less than about 1.0 μg/mL, less than about 0.5 μg/mL, or less than about 0.1 μg/mL, of furfural (w/v) after storage under room temperature, intermediate, and/or accelerated conditions for 1-24 months, e.g., 1 month, 2 months, 3 months, 6 months, 9 months, 12 months, 18 months, or 24 months. A stable ketamine composition additionally may refer to a composition that remains safe and effective and contains furfural present in an amount of about 0.001 μg/mL or more, e.g., about 0.005 μg/mL or more, about 0.01 μg/mL or more, about 0.05 μg/mL or more, about 0.1 μg/mL or more, about 0.2 μg/mL or more, about 0.5 μg/mL or more, about 1 μg/mL or more, or about 3 μg/mL or more, w/v of the composition, after storage under room temperature, intermediate, and/or accelerated conditions for 1-24 months, e.g., 1 month, 2 months, 3 months, 6 months, 9 months, 12 months, 18 months, or 24 months. A stable ketamine composition also may refer to a composition that contains furfural present in an amount bounded by any two of the aforementioned endpoints. For example, a stable ketamine composition additionally may refer to a composition that contains from about 0.001 μg/mL to about 50 μg/mL, from about 0.05 μg/mL to about 10 μg/mL, from about 0.05 μg/mL to about 5 μg/mL, from about 0.1 μg/mL to about 10 μg/mL, from about 0.1 μg/mL to about 1.5 μg/mL, from about 0.01 μg/mL to about 50 μg/mL, or from about 0.05 μg/mL to about 2 μg/mL of furfural w/v of the composition after storage under room temperature, intermediate, and/or accelerated conditions for 1-24 months, e.g., 1 month, 2 months, 3 months, 6 months, 9 months, 12 months, 18 months, or 24 months.

In some embodiments, the ketamine composition of the invention is stable for at least about 9 months, e.g., at least about 12 months, at least about 18 months, at least about 24 months, or at least about 36 months at room temperature (e.g., at 25±2° C.) or at refrigerated temperature (e.g., at 5±3° C.). The invention also includes embodiments in which the ketamine composition of the invention is stable for at least about 1 month, e.g., at least about 2 months, at least about 3 months, at least about 6 months, at least about 9 months, or at least about 12 months under intermediate (e.g., at 30° C.±2° C./65% RH±5% RH) and/or accelerated (e.g., at 40° C.±2° C./75% RH±5% RH) storage conditions.

Methods for determining the stability of a composition of the invention with respect to a given parameter are well-known in the art. For example, ketamine content, individual impurities and total impurities may be assessed by high-performance liquid chromatography (HPLC) or thin layer chromatography (TLC). Unless indicated otherwise, a percentage amount ketamine, any individual impurity, or total impurities reported herein in the formulation is determined by a peak area percent method using HPLC, and nitrosamines (e.g., NNK) are determined by liquid chromatography tandem mass spectrometry (LC-MS/MS).

In some embodiments, a stable ketamine composition may refer to a composition that is colorless, or colorless to slightly yellow, after storage under room temperature and/or accelerated conditions. The color of the composition may be determined, for example, by a United States Pharmacopoeia (USP) or European Pharmacopoeia (Ph. Eur.) color method.

The composition of the invention may be administered by injection, e.g., intravenously or intramuscularly, to produce and/or maintain anesthesia, e.g., in a human patient, in a manner similar to which Ketalar® is administered for its approved indications and uses.

The invention also provides a pharmaceutical product which includes a container and the composition of the invention as described herein aseptically sealed in the container. Suitable containers may include, for example, a vial, ampule, bottle, bag, cartridge, or a syringe used in the pharmaceutical industry for storing an injectable dosage form of a drug. The container can be made of glass or a synthetic polymer. The synthetic polymer may include an organic polymer such as, for example, an organic polymer which includes a polyethylene, a polypropylene, a cyclic olefin polymer (COP), or a cyclic olefin copolymer (COC). In some embodiments, the container includes COC. One or more surfaces of the container may be treated with a compound, e.g., to limit reactivity with one or more components of the composition of the invention. For example, the container may be treated with a silicone. By way of further example, the container may be treated with a sulfur-containing compound, e.g., ammonium sulfate. However, the invention also includes embodiments in which the container is not treated.

In some embodiments, the container includes a syringe. The syringe barrel may include or be made of, e.g., glass or plastic. A suitable plastic syringe may include a syringe barrel which includes or is made of an organic polymer such as, e.g., a polyethylene, a polypropylene, COP, or COC. In some embodiments, the plastic syringe barrel may include COC. Non-limiting examples of syringes suitable for use in the present invention are described in US Patent Application Publication No. 2015/0273133 which is incorporated herein by reference in its entirety.

The invention also includes embodiments in which the container includes a vial. The vial may be made of any suitable material, which may include, for example, glass or plastic. The glass vial may include, e.g., a transparent glass vial or a light protective glass vial.

The pharmaceutical container may be sealed, e.g., by way of a closure, such as, e.g., a stopper, valve, plunger, and/or tip cap. In some embodiments, the closure may include an inert material such as, e.g., rubber or plastic. The closure also may be coated, e.g., with a silicone polymer or a fluoropolymer. However, the invention also includes embodiments which include a container in which the closure is not coated. Non limiting examples of materials that may be used in suitable closures include, for example, bromobutyl rubber, chlorobutyl rubber, and coated versions thereof.

The invention accordingly provides, for example, a syringe that includes the stable, ready-to-administer ketamine composition described herein, wherein the syringe barrel includes COC and the stopper includes bromobutyl rubber.

In some embodiments, the container is a syringe and further comprise a tamper evidence tip cap cover, such as the syringe packaging system described in U.S. Pat. Nos. 10,661,030, 11,305,072, 11,964,142, 12,171,992, and 12,403,262, which are incorporated herein by reference in their entireties.

In other embodiments, the container is a bottle or bag, e.g., a flexible, multi-layered bag. The bag may include a material which is chemically inert to the composition, sterilizable, and weldable. Such materials may include, without limitation, polyolefin polymers (e.g., a polyethylene or polypropylene), cycloolefin polymers or cycloolefin copolymers, polycarbonates, styrene polymers, and block co-polymers thereof. In some embodiments, a polyolefin may be combined with an elastomeric polymer, such as, e.g., a styrene-ethylene/butylene-styrene-triblock polymer (SEBS), a styrene-ethylene/propylene-styrene-triblock polymer (SEPS), a styrene-butadiene-styrene-triblock polymer (SBS), and/or a styrene-isoprene-styrene triblock polymer (SIS). In certain embodiments, the container is a flexible, multi-layered bag wherein the innermost layer comprises polypropylene and SEBS, such as a bag marketed under the tradename, FREEFLEX™. In other embodiments, the innermost layer of the multi-layered bag comprises a polymer of cyclic olefin such as cycloolefin homopolymer or cycloolefin copolymer or mixture thereof. In yet other embodiments, the innermost layer of the multi-layered bag comprises ethylene-vinyl acetate copolymer. Suitable flexible bags are described in U.S. Pat. Nos. 5,783,269, 7,875,016, 8,162,915, 7,828,787, 8,118,802, 11,883,364, 12,005,026, and/or 12,390,397, which are incorporated herein by reference in their entireties. Other flexible polymeric containers suitable for use with a formulation according to the invention may include, without limitation, GALAXY™, VIAFLO™, INTRAVIA™, and EXCEL™ containers.

If desired, the container may be further contained or enclosed within a secondary packaging system to minimize permeation of oxygen into the container (primary container), especially for primary containers, e.g., vials, pre-filled syringes, bags, etc., that may have relatively high oxygen permeability. If desired, the secondary packaging system may further include a suitable oxygen absorber, e.g., within or outside of the secondary packaging (e.g., as an oxygen barrier and/or scavenger), to minimize oxygen levels inside of the secondary packaging and outside of the primary container. Suitable secondary packaging systems may include, for example, those described in U.S. Pat. No. 10,214,338, which describes secondary packaging systems for oxygen-sensitive drugs contained, e.g., within a syringe, cartridge, vial, or other drug storage container. In other embodiments, the secondary packaging system is a tray configured to hold multiple primary containers (e.g., vials or syringes) and having oxygen barrier properties.

The invention further provides a process for preparing the composition of the invention as described herein, which method generally includes:

- dissolving a tonicity agent as described herein in water,
- dissolving a nitrite scavenger as described herein in the water, and
- dissolving ketamine or pharmaceutically acceptable salt thereof as described herein in the water.

The water used in the process of the invention may include any suitable grade of water used in formulating injectable drugs. In some embodiments, the water used in the process of the invention is Water for Injection, USP.

The process of the invention optionally includes adding one or more pH adjusters, e.g., HCl and/or NaOH, to the composition if needed to achieve a desired pH. In some embodiments, HCl and/or NaOH may be added as needed to achieve a pH of, e.g., about 4.5-4.6, as described herein. If present, the pH adjuster can be added at any one or more stages of the process, e.g., before and/or after adding the tonicity agent, before and/or after adding the nitrite scavenger, and/or before and/or after adding the ketamine.

The dissolution of tonicity agent, nitrite scavenger, and ketamine or pharmaceutically acceptable salt may be performed in any order. In some embodiments, the process of the invention may include dissolving, in a suitable volume of water, the tonicity agent, then the nitrite scavenger, and then the ketamine or pharmaceutically acceptable salt thereof, then optionally adding additional water as needed to achieve a desired final volume.

In certain embodiments, the process for preparing the composition of the invention occurs in an inert environment which may be achieved in any suitable manner, e.g., in a manner that serves to remove oxygen from and/or minimize oxygen levels in the environment in which with process is performed. An inert environment may be achieved, for example, by purging the water and/or atmosphere in which the process is performed with an inert gas, e.g., nitrogen or argon. For example, an inert environment may be achieved by bubbling or sparging an inert gas such as, e.g., nitrogen or argon, into the water during the process of the invention to remove oxygen from or minimize oxygen levels in the water and surrounding atmospheric environment while the process is being performed.

In certain embodiments, the process for preparing the composition of the invention is carried out under conditions that minimize exposure to light. This can include shielding the environment from ambient light during weighing, transferring, and mixing steps. A light-protected environment may be provided, for example, by using opaque or light-blocking containers, covering equipment surfaces, and limiting illumination to low-intensity or filtered light. For example, the process may be performed in an environment where containers and vessels substantially prevent light penetration while the process is being performed.

In certain embodiments, the process for preparing the composition includes mixing components in a specific order to promote stability and minimize impurity formation. For example, the tonicity agent (e.g., sodium chloride) can be dissolved in water first, followed by dissolution of a nitrite scavenger (e.g., ascorbic acid), and then dissolution of ketamine or a pharmaceutically acceptable salt thereof. Mixing the tonicity agent and nitrite scavenger before the ketamine can help reduce impurity formation, including nitrosamine-related species. A pH-adjusting agent may be introduced at any suitable stage to achieve the desired pH. In a preferred embodiment, the nitrite scavenger is added before ketamine or a pharmaceutically acceptable salt thereof to neutralize nitrosating agents that may be present in the formulation.

In some embodiments, the process of the invention includes:

dissolving, in an inert environment, sodium chloride in water in an amount sufficient to achieve a final concentration of from about 6 mg/mL to about 7 mg/mL sodium chloride in the composition, dissolving, in an inert environment, ascorbic acid in the water in an amount sufficient to achieve a final concentration of from about 0.1 μg/mL to about 10 mg/mL ascorbic acid in the composition, and dissolving, in an inert environment, ketamine hydrochloride in the water in an amount sufficient to achieve a final concentration equivalent to about 10 mg/mL of ketamine free base in the composition, wherein the final concentration of ascorbic acid achieved in the composition includes any exemplary concentrations and ranges of concentrations of ascorbic as described herein, e.g., from about 0.1 μg/mL to about 10 mg/mL ascorbic acid, from about 0.5 g/mL to about 2.0 mg/mL ascorbic acid, from about 0.001 mg/mL to about 1.0 mg/mL ascorbic acid, from about 0.002 mg/mL to about 1.0 mg/mL ascorbic acid, from about 0.005 mg/mL to about 1.0 mg/mL ascorbic acid, from about 0.005 mg/mL to about 0.5 mg/mL ascorbic acid, from about 0.05 mg/mL to about 0.5 mg/mL ascorbic acid, from about 0.05 mg/mL to about 0.2 mg/mL ascorbic acid, from about 0.05 mg/mL to about 0.1 mg/mL ascorbic acid, from about 0.1 mg/mL to about 0.2 mg/mL ascorbic acid, about 0.1 μg/mL ascorbic acid, about 0.5 μg/mL ascorbic acid, about 0.001 mg/mL ascorbic acid, about 0.005 mg/mL ascorbic acid, about 0.05 mg/mL ascorbic acid, about 0.1 mg/mL ascorbic acid, about 0.2 mg/mL ascorbic acid, about 0.5 mg/mL ascorbic acid, and about 1.0 mg/mL ascorbic acid.

If desired, the process of the invention may include initially dissolving the tonicity agent, nitrite scavenger, and ketamine or pharmaceutically acceptable salt thereof in about 80% of the final volume water used in the composition, then adding to the solution the remaining quantity of water needed to achieve the final volume of the composition (Q.S.). The method the invention may thus include, for example, dissolving in an inert environment and in any suitable order, the tonicity agent, nitrite scavenger, and ketamine or pharmaceutically acceptable salt thereof in a portion of the water used in the composition, e.g., in about 80% of the final volume of water used in the composition, optionally adjusting the pH to a desired range, and then adding the remaining quantity of water needed to achieve the final volume of the composition (Q.S.).

In some embodiments, the process of the invention includes performing the following steps in an inert environment:

dissolving, in a portion of the water used in the composition, e.g., in about 80% of the final volume water used in the composition, sodium chloride in an amount sufficient to achieve a final concentration of from about 6 mg/mL to about 7 mg/mL sodium chloride in the composition, dissolving ascorbic acid in the water in an amount sufficient to achieve a final concentration of from about 0.1 μg/mL to about 10 mg/mL ascorbic acid in the composition, dissolving ketamine hydrochloride in the water in an amount sufficient to achieve a final concentration equivalent to about 10 mg/mL of ketamine free base in the composition, and adding to the solution the remaining quantity of water needed to achieve the final volume of the composition, wherein the final concentration of ascorbic acid achieved in the composition includes any exemplary concentrations and ranges of concentrations of ascorbic as described herein, e.g., from about 0.1 μg/mL to about 10 mg/mL ascorbic acid, from about 0.5 g/mL to about 2.0 mg/mL ascorbic acid, from about 0.001 mg/mL to about 1.0 mg/mL ascorbic acid, from about 0.002 mg/mL to about 1.0 mg/mL ascorbic acid, from about 0.005 mg/mL to about 1.0 mg/mL ascorbic acid, from about 0.005 mg/mL to about 0.5 mg/mL ascorbic acid, from about 0.05 mg/mL to about 0.5 mg/mL ascorbic acid, from about 0.05 mg/mL to about 0.2 mg/mL ascorbic acid, from about 0.05 mg/mL to about 0.1 mg/mL ascorbic acid, from about 0.1 mg/mL to about 0.2 mg/mL ascorbic acid, about 0.1 μg/mL ascorbic acid, about 0.5 μg/mL ascorbic acid, about 0.001 mg/mL ascorbic acid, about 0.005 mg/mL ascorbic acid, about 0.05 mg/mL ascorbic acid, about 0.1 mg/mL ascorbic acid, about 0.2 mg/mL ascorbic acid, about 0.5 mg/mL ascorbic acid, and about 1.0 mg/mL ascorbic acid.

The final composition produced by the inventive process may be aseptically filled into any suitable container(s) as described herein. The invention thus provides a pharmaceutical product as described herein, prepared by aseptically filling the composition prepared according to the inventive process into a suitable container as described herein, and sealing in the container to provide the pharmaceutical product. Suitable containers may include any suitable container such as, for example, vials, ampules, bottles, bags, cartridges and/or prefilled syringes as described herein. Preferably, the composition of the invention is manufactured using aseptic processing techniques and filled into a sterilized container, such that terminal sterilization is not required. In some embodiments, the composition is sterilized by filtration prior to filling into the container, such as by sterile filtration through a membrane filter. In some embodiments, the container is sterilized by radiation-based (e.g., gamma, X-ray, or e-beam) technology. In other embodiments, the container is sterilized by gas-based (e.g., ethylene oxide) technology. In yet other embodiments, the container is sterilized by thermal sterilization. If needed, the container may be further contained or enclosed within a secondary packaging system as described herein. If desired, any secondary packaging that is used may further include a suitable oxygen absorber, e.g., within or outside of the secondary packaging, as described herein.

In certain embodiments, sterilization is performed during the aseptic filling process, wherein the composition is passed through a sterilizing filter assembly immediately prior to being filled into a pre-sterilized container. The sterilizing filter assembly may comprise one or more sterilizing-grade membrane filter suitable for pharmaceutical use. In some embodiments, the assembly includes multiple filters arranged in series, such as two filters connected in series, although other configurations may be employed. The composition is aseptically transferred through the sterilizing filter assembly under controlled environmental conditions and directly filled into a pre-sterilized container. Suitable containers may include, for example, vials, flexible bags, or syringes as further described hereinabove, each of which may be sealed to maintain sterility and optionally enclosed within secondary packaging to provide additional protection against oxygen or light exposure. The one or more sterilizing-grade filter may include, for example, filters having a nominal pore size of about 0.2 μm. In some embodiments, the one or more sterilizing-grade filter comprises a polyvinylidene fluoride (PVDF) membrane. In certain embodiments, the sterilizing filter may be provided as a 4-inch sterilizing-grade membrane filter. Prior to use, the one or more sterilizing-grade filter may be preconditioned by soaking for a period of time, e.g., at least about 30 minutes, and flushing with a suitable volume of solution to remove extractables and ensure wetting of the membrane.

If desired, the composition or pharmaceutical product of the invention may be terminally sterilized by thermal sterilization. For example, thermal sterilization may be performed using water as a sterilizing medium. For sterilizing with water as the sterilization medium, the temperature of the water is preferably at least about 100° C., e.g., at least about 110° C., e.g., at least about 120° C. The thermal sterilization may be performed at a pressure of at least about 1 bar (100 kilopascal), for example, at least about 1.5 bar (150 kilopascal), at least about 1.7 bar (170 kilopascal), at least about 2 bar (200 kilopascal), at least about 3 bar (300 kilopascal), or at least about 4 bar (400 kilopascal). In some embodiments, thermal sterilization is performed at a pressure of from about 1 bar to about 4 bar, e.g., about 1-3 bar, about 1.5-2 bar, about 1.7-2 bar, or about 1.7-3 bar. Thermal sterilization may be carried out for at least about 10 minutes, e.g., for at least about 15 minutes, or for at least about 20 minutes.

The following examples further illustrate the invention but, of course, should not be construed as in any way limiting its scope.

Example 1

This example demonstrates a method of preparing an exemplary composition of the invention.

Water for Injection is filled into a suitable container using a volume of water that is approximately 80% of the final volume of the composition. Nitrogen gas is bubbled into the water in the container until the dissolved oxygen content is about 0.5 ppm, and nitrogen bubbling is continued until the compounding process is completed. When the dissolved oxygen content in the water is about 0.5 ppm, sodium chloride is added, with mixing, in an amount needed to achieve a final concentration of about 6 mg/mL to about 7 mg/mL sodium chloride, mixing is continued until the sodium chloride dissolves, and the pH is measured. Ascorbic acid is then added, with mixing, in an amount needed to achieve a final concentration of from about 0.005 mg/mL to about 1.0 mg/mL ascorbic acid, mixing is continued until the ascorbic acid dissolves, and the pH is measured, at which point the target pH is generally about 3.0-4.0. If needed, sodium hydroxide or HCl may be added to achieve the target pH of 4.5-7.0. Ketamine hydrochloride is then added slowly, with mixing, in an amount needed to achieve a final concentration equivalent to about 10 mg/mL of the free base, mixing is continued until the ketamine hydrochloride dissolves, and sodium hydroxide or HCl is added as needed to achieve a target pH of 4.5-4.6. Water for Injection is then added until the final volume is achieved, the solution is mixed well until the desired uniformity is obtained, and nitrogen bubbling is stopped to produce a composition of the invention (pH about 4.5-4.6).

The components of the composition are summarized in Table 2.

TABLE 2

| Ingredients | Concentration per mL |
|---|---|
| Ketamine* | 10 mg |
| Sodium Chloride | 6.6 mg |
| Ascorbic Acid | 0.005 mg-1 mg |
| Sodium Hydroxide | As needed |
| Hydrochloric Acid | As needed |
| Water for Injection | Q.S. to final volume |

*Ketamine hydrochloride (approximately 11.53 mg/mL) equivalent to 10 mg/mL of ketamine free base.

Example 2

This example demonstrates an exemplary product of the invention. An exemplary composition of the invention is prepared as described in Example 1. The components of the composition are summarized in Table 3.

TABLE 3

| Ingredients | Concentration per mL |
|---|---|
| Ketamine* | 10 mg |
| Sodium Chloride | 6.6 mg |
| Ascorbic Acid | 0.05 mg |
| Sodium Hydroxide | As needed |
| Hydrochloric Acid | As needed |
| Water for Injection | Q.S. to final volume |

*Ketamine hydrochloride (approximately 11.53 mg/mL) equivalent to 10 mg/mL of ketamine free base.

The composition is aseptically filled into 5 cc clear glass vials, each filled with 5 mL of the composition, and the vials are sealed with West 4432/50 Flurotec coated chlorobutyl rubber stoppers.

Example 3

This example demonstrates the stability of exemplary compositions of the invention. Exemplary formulations of the invention were prepared as described in Example 1. The components of the compositions prepared and tested, excluding the NaOH and/or HCl added as needed for pH adjustment in Groups B-G (invention), are summarized in Table 4.

TABLE 4

| Formulation | Ingredients | Concentration per mL | Function |
|---|---|---|---|
| Group A (Control) | Ketamine* | 10 mg | Active |
| | Sodium Chloride | 6.6 mg | Tonicity Adjuster |
| | Water for Injection | Q.S. to final volume | Drug Vehicle |
| Group B | Ketamine* | 10 mg | Active |
| | Sodium Chloride | 6.6 mg | Tonicity Adjuster |

TABLE 4-continued

| Formulation | Ingredients | Concentration per mL | Function |
|---|---|---|---|
| | Ascorbic Acid | 0.2 mg | Nitrite Scavenger |
| | Water for Injection | Q.S. to final volume | Drug Vehicle |
| Group C | Ketamine* | 10 mg | Active |
| | Sodium Chloride | 6.6 mg | Tonicity Adjuster |
| | Ascorbic Acid | 0.1 mg | Nitrite Scavenger |
| | Water for Injection | Q.S. to final volume | Drug Vehicle |
| Group D | Ketamine* | 10 mg | Active |
| | Sodium Chloride | 6.6 mg | Tonicity Adjuster |
| | Ascorbic Acid | 0.05 mg | Nitrite Scavenger |
| | Water for Injection | Q.S. to final volume | Drug Vehicle |
| Group E | Ketamine* | 10 mg | Active |
| | Sodium Chloride | 6.6 mg | Tonicity Adjuster |
| | Ascorbic Acid | 0.01 mg | Nitrite Scavenger |
| | Water for Injection | Q.S. to final volume | Drug Vehicle |
| Group F | Ketamine* | 10 mg | Active |

TABLE 4-continued

| Formulation | Ingredients | Concentration per mL | Function |
|---|---|---|---|
| | Sodium Chloride | 6.6 mg | Tonicity Adjuster |
| | Ascorbic Acid | 0.005 mg | Nitrite Scavenger |
| | Water for Injection | Q.S. to final volume | Drug Vehicle |
| Group G | Ketamine* | 10 mg | Active |
| | Sodium Chloride | 6.6 mg | Tonicity Adjuster |
| | Ascorbic Acid | 1.0 mg | Nitrite Scavenger |
| | Water for Injection | Q.S. to final volume | Drug Vehicle |

*Ketamine hydrochloride (approximately 11.53 mg/mL) equivalent to 10 mg/mL of ketamine free base.

N-nitrosoketamine (NNK) impurity concentration was measured and ketamine content was assayed in the compositions of Group A (control) and Groups B-F (invention) during storage at 25° C. and during storage at 40° C. in Schott PopPac™ 5 mL cyclic olefin copolymer (COC) plastic syringes, each sealed with a Datwyler Pharma FM457/2 uncoated bromobutyl rubber stopper and FM257 uncoated bromobutyl tip cap. Each syringe was aseptically filled with 5 mL of the composition.

The samples were analyzed by HPLC-MS/MS for NNK content and by HPLC for ketamine assay. For NNK content, the HPLC conditions were as follows:

Mobile Phase A: 0.1% Formic Acid in Water

Mobile Phase B: 0.1% Formic Acid in Methanol

Column: Zorbax Eclipse Plus C18 Rapid Resolution, 2.1×50 mm, 1.8 m

Column temperature: 28° C.

Flow rate: 0.35 mL/min

Injection volume: 10 μL

Autosampler temperature: 5° C.

Separation mode: Gradient

Run time: 12 minutes

| Gradient Conditions | | |
|---|---|---|
| Time (min) | % Mobile Phase A | % Mobile Phase B |
| 0 | 65 | 35 |
| 7 | 10 | 90 |
| 7.1 | 65 | 35 |
| 10 | 65 | 35 |

Detection: MS/MS

Mass Spectrometer: Sciex 5600 TripleTOF or Agilent 6495D Triple Quadrupole; exemplary parameters for the Agilent MS are as follows.

Polarity: Positive

Scan Type: MRM

| Precursor ion | MS1 Res | Product ion | MS2 Res | Dwell | Fragmentator | Collision Energy | Cell Accelerator Voltage |
|---|---|---|---|---|---|---|---|
| 267.1 m/z | Unit | 125 m/z | Unit | 100 ms | 166 V | 30 V | 5 V |
| 275.1 m/z | Unit | 127 m/z | Unit | 100 ms | 166 V | 32 V | 5 V |

| Ion Source | AJS ESI |
|---|---|
| Gas Temperature | 200° C. |
| Gas Flow | 13 L/min |
| Nebulizer | 34 psi |
| Capillary Voltage | 3600 V |
| Sheath Gas Temperature | 250° C. |
| Sheath Gas Flow | 12 L/min |
| Nozzle Voltage | 200 V |

Nitrosoketamine (267.1→125.0) was quantitated in finished product samples against a calibration curve using N-Nitrosoketamine-d8 (275.1→127.0) as an internal standard.

For ketamine assay, the HPLC conditions were as follows:

Buffer: 20 mL/L Triethylamine+31.2 g/L Citric acid in water

Mobile Phase A: Buffer:Acetonitrile:Methanol (90:7.5:2.5)

Mobile Phase B: Water:Acetonitrile:Methanol (30:52.5:17.5)

Column: Waters Cortecs C8 4.6×100 mm, 2.7 μm

Column temperature: 28±2° C.

Flow rate: 1.2 mL/min

Injection volume: 15 μL

Autosampler temperature: 5±3° C.

Detection: UV at 270 nm

Separation mode: Gradient

Run time: 45 minutes

| Gradient Conditions | | |
|---|---|---|
| Time (min) | % Mobile Phase A | % Mobile Phase B |
| 0 | 100 | 0 |
| 30 | 0 | 100 |
| 35 | 0 | 100 |

-continued

| Gradient Conditions | | |
|---|---|---|
| Time (min) | % Mobile Phase A | % Mobile Phase B |
| 36 | 100 | 0 |
| 45 | 100 | 0 |

Ketamine was quantitated against an external calibration curve. The results are summarized in Table 5.

TABLE 5

| Formulation | Storage Conditions | | pH | Visual Appearance | NNK Content (ppb) | Ketamine Assay (%) |
|---|---|---|---|---|---|---|
| Group A (Control) (Initial pH 4.49) | 25° C. | 2 weeks | 4.55 | Clear, Colorless | 337 | 98.6 |
| | | 1 month | 4.45 | Clear, Colorless | 1222 | 99.2 |
| | | 6 weeks | NT | Clear, Colorless | NT | 100.5 |
| | | 2 months | 4.38 | Clear, Colorless | 522 | 100.2 |
| | | 3 months | 4.38 | Clear, Colorless | 678 | NT |
| | | 6 months | 4.4 | Clear, Colorless | 626 | 100.1 |
| | 40° C. | 2 weeks | 4.4 | Clear, Colorless | 898 | 99.2 |
| | | 1 month | 4.33 | Clear, Colorless | 614 | 98.8 |
| | | 6 weeks | 4.22 | Clear, Colorless | 949 | 100.8 |
| | | 2 months | 4.15 | Clear, Colorless | 812 | 99.8 |
| | | 3 months | 4.17 | Clear, Pale Yellow | 1098 | NT |
| | | 6 months | 4.08 | Clear, Colorless | 1058 | 100.1 |
| Group B (Initial pH 4.53) | 25° C. | 2 weeks | 4.44 | Clear, Colorless | 141 | 99.6 |
| | | 1 month | 3.85 | Clear, Colorless | 154 | 99 |
| | | 6 weeks | NT | NT | NT | 100.4 |
| | | 2 months | 3.71 | Clear, Pale Yellow | 173 | 99.5 |
| | | 3 months | 3.71 | Clear, Pale Yellow | 152 | 99.1 |
| | | 6 months | 3.82 | Clear, Pale Yellow | 116 | 99.2 |
| | 40° C. | 2 weeks | 3.95 | Clear, Pale Yellow | 157 | 98.7 |
| | | 1 month | 3.87 | Clear, Pale Yellow | 178 | 99.2 |
| | | 6 weeks | 3.69 | Clear, Pale Yellow | 164 | 100.5 |
| | | 2 months | 3.82 | Clear, Pale Yellow | 226 | 99.5 |
| | | 3 months | 3.85 | Clear, Pale Yellow | 260 | 99 |
| | | 6 months | NT | NT | 311 | NT |
| Group C (Initial pH 4.53) | 25° C. | 2 weeks | 4.46 | Clear, Colorless | 152 | 99.1 |
| | | 1 month | 3.89 | Clear, Colorless | 152 | 99.4 |
| | | 6 weeks | NT | NT | NT | 100.5 |
| | | 2 months | 3.86 | Clear, Pale Yellow | 176 | 99.6 |
| | | 3 months | 3.86 | Clear, Pale Yellow | 151 | 99.1 |
| | | 6 months | 4.06 | Clear, Pale Yellow | 121 | 100.4 |
| | 40° C. | 2 weeks | 4.01 | Clear, Pale Yellow | 156 | 99.3 |
| | | 1 month | 3.89 | Clear, Pale Yellow | 245 | 99.6 |
| | | 6 weeks | NT | Clear, Pale Yellow | NT | 100.5 |
| | | 2 months | 3.85 | Clear, Pale Yellow | 277 | 99.7 |
| | | 3 months | 3.83 | Clear, Pale Yellow | 349 | 98.9 |
| | | 6 months | 3.8 | Clear, Pale Yellow | 334 | 99.1 |
| Group D (Initial pH 4.53) | 25° C. | 0 hours | 4.53 | NT | 243 | 100.3 |
| | | 24 hours | NT | NT | 177 | 100.9 |
| | | 48 hours | NT | NT | 156 | 99.8 |
| | | 72 hours | NT | NT | 193 | 101 |
| | | 1 month | 4.05 | Clear, Colorless | 139 | 100.3 |
| | | 2 months | NT | NT | 194 | 100.6 |
| | | 3 months | 4.67 | Clear, Colorless | 141 | 100.1 |
| | | 6 months | 3.93 | Clear, Pale Yellow | 214 | 99.5 |
| | | 12 months | 4.53 | Clear, Colorless | 152 | 100.5 |
| | 40° C. | 2 weeks | 4.17 | Clear, Colorless | 194 | 101 |
| | | 1 month | 4.36 | Clear, Colorless | 306 | 100 |
| | | 2 months | 3.96 | Clear, Colorless | 497 | 100.3 |
| | | 3 months | 4.08 | Clear, Colorless | 449 | 100.4 |
| | | 6 months | 4.06 | Clear, Pale Yellow | 611 | 100.8 |
| Group E (Initial pH 4.54) | 25° C. | 0 hours | 4.54 | NT | 239 | 100.6 |
| | | 24 hours | NT | NT | 169 | 100.6 |
| | | 48 hours | NT | NT | 179 | 100.1 |
| | | 72 hours | NT | NT | 204 | 100.5 |
| | | 1 month | 4.68 | Clear, Colorless | 213 | 99.6 |
| | | 2 months | NT | NT | 323 | 100.8 |
| | | 3 months | 4.29 | Clear, Colorless | 298 | 101.1 |
| | | 6 months | 4.17 | Clear, Colorless | 374 | 100.8 |
| | | 12 months | 4.44 | Clear, Colorless | 266 | 100.9 |
| | 40° C. | 2 weeks | 4.43 | Clear, Colorless | 191 | 100.6 |
| | | 1 month | 4.25 | Clear, Colorless | 415 | 99.7 |
| | | 2 months | 4.10 | Clear, Colorless | 748 | 101 |

TABLE 5-continued

| Formulation | Storage Conditions | | pH | Visual Appearance | NNK Content (ppb) | Ketamine Assay (%) |
|---|---|---|---|---|---|---|
| | | 3 months | 4.12 | Clear, Colorless | 685 | 100.8 |
| | | 6 months | 3.94 | Clear, Colorless | 702 | 101.1 |
| Group F (Initial pH 4.51) | 25° C. | 0 hours | 4.51 | NT | 240 | 100.6 |
| | | 24 hours | NT | NT | 168 | 101.2 |
| | | 48 hours | NT | NT | 223 | 101 |
| | | 72 hours | NT | NT | 278 | 100.4 |
| | | 1 month | 4.40 | Clear, Colorless | 211 | 99.3 |
| | | 2 months | NT | NT | 402 | 99.9 |
| | | 3 months | 4.41 | Clear, Colorless | 325 | 100.4 |
| | | 6 months | 4.23 | Clear, Colorless | 407 | 99.9 |
| | | 12 months | 4.12 | Clear, Colorless | 318 | 100.9 |
| | 40° C. | 2 weeks | 4.32 | Clear, Colorless | 1848 | 100.2 |
| | | 1 month | 4.25 | Clear, Colorless | 810 | 99.5 |
| | | 2 months | NT | NT | 938 | 100.2 |
| | | 3 months | 4.14 | Clear, Colorless | 762 | 100.7 |
| | | 6 months | 3.97 | Clear, Colorless | 821 | 100.0 |
| Group G (Initial pH 4.55) | 25° C. | 2 weeks | 4.54 | Clear, Colorless | 137 | 97.0 |
| | | 1 month | 4.23 | Clear, Pale Yellow | 155 | 99.5 |
| | | 6 weeks | NT | NT | NT | 96.3 |
| | | 2 months | NT | Clear, Bright Yellow | 169 | 94.3 |
| | | 3 months | NT | Clear, Bright Yellow | 133 | 94.5 |
| | | 6 months | NT | Clear, Bright Yellow | 89 | 94.6 |
| | 40° C. | 2 weeks | 4.11 | Clear, Yellow | 152 | 95.3 |
| | | 1 month | 4.06 | Clear, Dark Yellow | 172 | 95.1 |
| | | 6 weeks | NT | NT | NT | 95.4 |
| | | 2 months | NT | Hazy, Bright Yellow | 162 | 95.2 |
| | | 3 months | NT | Hazy, Bright Yellow | 182 | 93.7 |
| | | 6 months | NT | Hazy, Bright Yellow | 331 | 93.9 |

These results show that the composition of the invention provides an improvement in formulation stability as evidenced by the reduction in NNK impurity levels relative to control during storage at 25° C. and 40° C.

Example 4

This example demonstrates the stability of exemplary compositions of the invention comprising ascorbic acid as a nitrite scavenger as compared to compositions comprising glycine. The compositions were prepared as described in Example 1 except that some compositions contained glycine instead of ascorbic acid. The components of the compositions prepared and tested are summarized in Table 6.

TABLE 6

| Formulation | Ingredients | Concentration per mL | Function |
|---|---|---|---|
| Control | Ketamine* | 10 mg | Active |
| | Sodium Chloride | 6.6 mg | Tonicity Adjuster |
| | Water for Injection | Q.S. to final volume | Drug Vehicle |
| Ascorbic Acid | Ketamine* | 10 mg | Active |
| | Sodium Chloride | 6.6 mg | Tonicity Adjuster |
| | Ascorbic Acid | 0.2 mg | Nitrite Scavenger |
| | HCl | As needed | pH Adjuster |
| | NaOH | As needed | pH Adjuster |
| | Water for Injection | Q.S. to final volume | Drug Vehicle |
| Glycine | Ketamine* | 10 mg | Active |
| | Sodium Chloride | 6.6 mg | Tonicity Adjuster |
| | Glycine | 1 mg | Nitrite Scavenger |
| | HCl | As needed | pH Adjuster |
| | NaOH | As needed | pH Adjuster |
| | Water for Injection | Q.S. to final volume | Drug Vehicle |

*Ketamine hydrochloride (approximately 11.53 mg/mL) equivalent to 10 mg/mL of ketamine free base.

N-nitrosoketamine (NNK) impurity concentrations were determined and ketamine content assayed in the formulation during storage at 25° C. and during storage at 55° C. in 5 cc clear glass vials, each sealed with a West 4432/50 Flurotec-coated chlorobutyl rubber stopper. Each vial was aseptically filled with 5 mL of the composition, sealed, and optionally subjected to terminal sterilization (TS) at about 124° C. for 15 minutes. NNK impurity levels were determined as described in Example 3. The results are summarized in Table 7.

TABLE 7

| Formulation | Storage Conditions | | NNK Content (ppb) Non-TS | NNK Content (ppb) TS |
|---|---|---|---|---|
| Control | 25° C. | 2 weeks | 924 | 1921 |
| | | 1 month | 1327 | 3435 |
| | | 2 months | 1858 | 2826 |
| | | 3 months | 1551 | 3173 |
| | | 6 months | 1318 | 2264 |
| | | 9 months | 1691 | 2838 |
| | 55° C. | 2 weeks | 2129 | 2188 |
| | | 1 month | 2034 | 3435 |
| Ascorbic Acid | 25° C. | 2 weeks | 134 | 281 |
| | | 1 month | 148 | 479 |
| | | 2 months | 151 | 548 |
| | | 3 months | 176 | 648 |
| | | 6 months | 196 | 805 |
| | | 9 months | 113 | 807 |
| | 55° C. | 2 weeks | 702 | 4253 |
| | | 1 month | 993 | 3341 |
| Glycine | 25° C. | 2 weeks | 842 | 1819 |
| | | 1 month | 1960 | 1378 |
| | | 2 months | 1320 | 1437 |
| | | 3 months | 1734 | 1943 |
| | | 6 months | 1257 | 1599 |
| | | 9 months | 1204 | 1719 |
| | 55° C. | 2 weeks | 829 | 1468 |
| | | 1 month | 1508 | 2590 |

The results show that a composition of the invention containing ascorbic acid provides an improvement in NNK impurity levels relative to a control composition containing no nitrite scavenger or a composition containing glycine during storage at 25° C. and 55° C. NNK impurity levels were increased in all compositions following TS, although ascorbic acid still provided a protective effect relative to control or glycine during storage at 25° C.

Example 5

This example describes an exemplary method for measuring ascorbic acid and furfural in an exemplary composition or pharmaceutical product of the invention.

A sterile, injectable aqueous pharmaceutical composition comprising 10 mg/mL ketamine (as HCl), 6.6 mg/mL sodium chloride, and 0.01 mg/mL ascorbic acid, adjusted to pH of about 4.6 was prepared as described herein. Samples were tested for ascorbic acid and furfural contents by HPLC using the following conditions.

Mobile Phase A: 20 mM $KH_2PO_4$, pH 2.5
Mobile Phase B: 100% methanol
Diluent: degassed Mobile Phase A
Column: Agilent Poroshell 120 EC-C18 4.6×150 mm, 2.7 μm
Column temperature: 20±1° C.
Flow rate: 1.0 mL/min
Injection volume: 5 μL
Autosampler temperature: 5° C.
Detection: UV at 278 nm
Needle Wash: 50% methanol in water
Separation mode: Gradient
Run time: 25 minutes Gradient Conditions

| Time (min) | % Mobile Phase A | % Mobile Phase B |
|---|---|---|
| 0 | 95 | 5 |
| 2.0 | 95 | 5 |
| 2.1 | 75 | 25 |
| 13.0 | 75 | 25 |
| 13.1 | 10 | 90 |
| 18.0 | 10 | 90 |
| 18.1 | 95 | 5 |
| 25.0 | 95 | 5 |

The results showed that the exemplary composition contained not more than about 0.012 mg/mL ascorbic acid and not more than about 2 μg/mL furfural.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A sterile, injectable pharmaceutical composition comprising a therapeutically effective amount of ketamine or a pharmaceutically acceptable salt thereof, ascorbic acid, a tonicity agent, and water,
- wherein the therapeutically effective amount of ketamine or the pharmaceutically acceptable salt thereof is present in an amount of about 0.1 mg/mL to about 10 mg/ml of ketamine free base,
- wherein ascorbic acid is present in an amount of about 0.005 mg/mL to about 1 mg/mL,
- wherein after 6 months of storage at room temperature, the composition (i) contains less than about 500 ppb of N-nitrosoketamine, (ii) retains at least about 95% of the initial amount of the ketamine free base, and (iii) has a pH of about 3.5 to about 5.5.

2. The composition of claim 1, comprising furfural in an amount of less than about 2% by weight of the ascorbic acid.

3. The composition of claim 1, comprising less than about 1.0% of total ketamine degradation products as determined by high performance liquid chromatography (HPLC).

4. A sterile, injectable pharmaceutical composition comprising ketamine hydrochloride at a concentration equivalent to about 0.1 mg/mL to about 10 mg/mL of ketamine free base, from about 0.005 mg/mL to about 0.2 mg/mL of ascorbic acid, a tonicity agent, and water,
- wherein after 6 months of storage at room temperature, the composition (i) contains less than about 500 ppb of N-nitrosoketamine, (ii) retains at least about 99% of the initial amount of the ketamine free base, and (iii) has a pH of about 3.5 to about 5.5.

5. The composition of claim 4, comprising ketamine hydrochloride at a concentration equivalent to about 10 mg/mL of the free base and from about 0.005 mg/mL to about 0.1 mg/mL of ascorbic acid, wherein the tonicity agent is sodium chloride, and the composition has a pH of about 4.0 to about 5.0.

6. The composition of claim 5, comprising from about 6 mg/mL to about 7 mg/mL sodium chloride, wherein following storage of the composition for 6 months at room temperature, the composition comprises less than about 500 ppb of N-nitrosoketamine, less than about 0.2% of any individual ketamine degradation product as determined by HPLC, less than about 1.0% of total ketamine degradation products as determined by HPLC, and furfural in an amount of less than about 2% by weight of the ascorbic acid.

7. The composition of claim 5, comprising about 0.01 mg/mL of ascorbic acid and about 6.6 mg/mL of sodium chloride.

8. The composition of claim 4, comprising furfural in an amount of less than about 2% by weight of the ascorbic acid.

9. The composition of claim 4, comprising less than about 1.0% of total ketamine degradation products as determined by HPLC.

10. A pharmaceutical product comprising a container and a composition aseptically sealed in the container, wherein the composition comprises ketamine hydrochloride at a concentration equivalent to about 0.1 mg/mL to about 10 mg/ml of ketamine free base, from about 0.005 mg/mL to about 0.2 mg/mL of ascorbic acid, a tonicity agent, and water, wherein after 6 months of storage at room temperature, the composition (i) contains less than about 500 ppb of N-nitrosoketamine, (ii) retains at least about 95% of the initial amount of the ketamine free base, and (iii) has a pH of about 3.5 to about 5.5.

11. The pharmaceutical product of claim 10, wherein the container is a vial, ampule, bottle, bag, cartridge, or a syringe.

12. The pharmaceutical product of claim 10, wherein the container is a syringe, and the composition comprises ketamine hydrochloride at a concentration equivalent to about 10 mg/mL of the free base and from about 0.005 mg/mL to about 0.1 mg/mL of ascorbic acid, wherein the tonicity agent is sodium chloride, and the composition has a pH of about 4.0 to about 5.0.

13. The pharmaceutical product of claim 12, wherein the syringe barrel comprises an organic polymer selected from the group consisting of polyethylene, a polypropylene, a cyclic olefin polymer (COP), and a cyclic olefin copolymer (COC), and the syringe stopper comprises bromobutyl rubber, chlorobutyl rubber, or a coated version thereof.

14. The pharmaceutical product of claim 13, comprising a tamper evidence tip cap cover.

15. The pharmaceutical product of claim 12, wherein the composition comprises about 0.01 mg/mL of ascorbic acid and about 6.6 mg/mL of sodium chloride.

16. The pharmaceutical product of claim 10, wherein the composition comprises from about 0.005 mg/mL to about 0.2 mg/ml of ascorbic acid and from about 6 mg/mL to about 7 mg/mL sodium chloride, wherein following storage of the composition for 6 months at room temperature, the composition comprises less than about 500 ppb of N-nitrosoketamine, less than about 0.2% of any individual ketamine degradation product as determined by HPLC, less than about 1.0% of total ketamine degradation products as determined by HPLC, and furfural in an amount of less than about 2% by weight of the ascorbic acid.

17. The pharmaceutical product of claim 16, wherein the syringe barrel comprises COP or COC, the syringe stopper comprises bromobutyl rubber, and the product comprises a tamper evidence tip cap cover.

18. The pharmaceutical product of claim 16, wherein the composition comprises about 0.01 mg/mL of ascorbic acid and about 6.6 mg/mL of sodium chloride.

* * * * *